United States Patent [19]
Bushek et al.

[11] Patent Number: 6,050,933
[45] Date of Patent: Apr. 18, 2000

[54] HEARING AID TRANSDUCER SUPPORT

[75] Inventors: Donald J. Bushek, Plymouth; Kai Kroll, Minnetonka, both of Minn.

[73] Assignee: St. Croix Medical, Inc., Minneapolis, Minn.

[21] Appl. No.: 09/188,769

[22] Filed: Nov. 9, 1998

Related U.S. Application Data

[63] Continuation of application No. 08/695,099, Aug. 7, 1996, Pat. No. 5,836,863.

[51] Int. Cl.⁷ .................................................. H04R 25/00
[52] U.S. Cl. ............................ 600/25; 128/898; 381/312; 181/135
[58] Field of Search .................. 600/25, 559; 607/55–57, 607/136, 137; 381/312, 322, 324, 328, 329; 181/129, 130, 134, 135

[56] References Cited

U.S. PATENT DOCUMENTS

| | | |
|---|---|---|
| 3,557,775 | 1/1971 | Mahoney . |
| 3,594,514 | 7/1971 | Wingrove . |
| 3,712,962 | 1/1973 | Epley . |
| 3,764,748 | 10/1973 | Branch et al. . |
| 3,931,648 | 1/1976 | Shea, Jr. . |
| 3,992,725 | 11/1976 | Homsy . |

(List continued on next page.)

FOREIGN PATENT DOCUMENTS

| | | |
|---|---|---|
| 263 254 A1 | 4/1988 | European Pat. Off. . |
| 28 34 891 A1 | 1/1980 | Germany . |
| WO 92/08330 | 5/1992 | WIPO . |
| WO 94/17645 | 8/1994 | WIPO . |

OTHER PUBLICATIONS

ÁWengen, M.D., D.F., et al., "Measurements of the Stapes Superstructure," Ann. Otol. Rhinol. Laryngology, 104:311–316, (1995).

Dormer, PhD., K.J., et al., "Selection of Biomaterials for Middle and Inner Ear Implants," Otolaryngologic Clinics Of North America, 28:17–27, (1995).

Dumon, T., et al., "Piezoelectric Middle Ear Implant: Experimental Results," Abstract of Paper Presented at International Symposium on Electronic Implants in Otology and Conventional Hearing Aids. Walt Disney World Swan, Abstract #35, (Nov. 11–14, 1993).

Fredrickson, M.D., J.M., et al., "Ongoing Investigations into an Implantable Electromagnetic Hearing Aid for Moderate to Severe Sensorineural Hearing Loss," Otolaryngologic Clinics of North America, 28:107–120, (1995).

Goode, M.D., R.L., et al., "New Knowledge About the Function of the Human Middle Ear: Development of an Improved Analog Model," American Journal of Otology, 15:145–154, (1994).

Goode, M.D., R.L., et al., "The History and Development of the Implantable Hearing Aid," Otolaryngologic Clinics of North America, 28:1–16, (1995).

(List continued on next page.)

*Primary Examiner*—Linda C. M. Dvorak
*Assistant Examiner*—David Ruddy
*Attorney, Agent, or Firm*—Patterson & Keough, P.A.

[57] ABSTRACT

A support for input and output transducers of a hearing aid is implanted in the middle ear. The support, which is attached to the mastoid bone, can be a single component or comprise two adjustable components. In one embodiment, an arm extends from the proximal end of the support towards an access hole created behind the outer ear, where the arm is attached for further stability. In another embodiment, the arm extends outside the access hole, where it is mounted subcutaneously to the mastoid bone with a mechanical fastener. The support provides positional adjustability, stability, and is invisible externally.

7 Claims, 6 Drawing Sheets

U.S. PATENT DOCUMENTS

| | | |
|---|---|---|
| 4,315,433 | 2/1982 | Edelman et al. . |
| 4,601,723 | 7/1986 | McGrew . |
| 4,628,907 | 12/1986 | Epley . |
| 4,728,327 | 3/1988 | Gersdorff . |
| 4,729,366 | 3/1988 | Schaefer . |
| 4,756,312 | 7/1988 | Epley . |
| 4,774,933 | 10/1988 | Hough et al. . |
| 4,776,322 | 10/1988 | Hough et al. . |
| 4,817,607 | 4/1989 | Tatge . |
| 4,840,178 | 6/1989 | Heide et al. . |
| 4,850,962 | 7/1989 | Schaefer . |
| 4,957,478 | 9/1990 | Maniglia . |
| 4,969,900 | 11/1990 | Fleischer . |
| 4,988,333 | 1/1991 | Engebretson et al. . |
| 5,012,520 | 4/1991 | Steeger . |
| 5,015,224 | 5/1991 | Maniglia . |
| 5,015,225 | 5/1991 | Hough et al. . |
| 5,163,957 | 11/1992 | Sade et al. . |
| 5,277,694 | 1/1994 | Leysieffer et al. . |
| 5,282,858 | 2/1994 | Bisch et al. . |
| 5,338,287 | 8/1994 | Miller et al. . |
| 5,360,388 | 11/1994 | Spindel et al. . |
| 5,370,689 | 12/1994 | Causse . |
| 5,411,467 | 5/1995 | Hortmann et al. . |
| 5,456,654 | 10/1995 | Ball . |
| 5,498,226 | 3/1996 | Lenkauskas . |
| 5,531,787 | 7/1996 | Lesinski et al. . |
| 5,554,096 | 9/1996 | Ball . |
| 5,558,618 | 9/1996 | Maniglia . |
| 5,624,376 | 4/1997 | Ball et al. . |

OTHER PUBLICATIONS

Gyo, K., et al., "Sound Pickup Utilizing an Implantable Piezoelectric Ceramic Bimorph Element: Application to the Cochlear Implant," American Journal of Otology, 5:273–276, (1984).

Gyo, K., et al., "Stapes Vibration Produced by the Output Transducer of an Implantable Hearing Aid," Archives of Otolaryngology Head and Neck Surgery, 113:1078–1081, (1987).

Jako, M.D., G.J., "Biomedical Engineering in Ear Surgery," Otolaryngologic Clinics of North America, 5:173–182, (1972).

Ko, PhD., W., "Engineering Principles of Mechanical Stimulation of the Middle Ear," Otolaryngologic Clinics of North America, 28:29–41, (1995).

Ko, PhD., W.H., "A Preliminary Study on the Implantable Middle Ear Hearing Aid,"I.E.E.E. 9th Annual Conference on Engineering in Medicine and Biology Society, (1987).

Kodera, M.D., et al., "Sound Evaluation of Partially Implantable Piezoelectric Middle Ear Implant: Comparative Study of Frequency Responses," Ear, Nose and Throat Journal, 73:108–111, (1994).

Lenkauskas, E., "Totally Implantable Hearing Aid Device," Transplants and Implants in Otology II, 371–375, (1991).

Maniglia, M.D., A.J., et al., "Electromagnetic Implantable Middle Ear Hearing Device of the Ossicular–Stimulating Type: Principles, Designs, and Experiments," Ann. Otol. Rhinol Laryngol, 97 (Suppl 136), part 2, (1988).

Maniglia, A.J., et al., "Contactless, Semi–Implantable Electromagnetic Hearing Device for the Treatment of Sensorineural Hearing Loss," Abstract of Paper Presented at International Symposium on Electronic Implants in Otology and Conventional Hearing Aids. Walt Disney World Swan, Abstract #29, (Nov. 11–14, 1993).

Maniglia, M.D., A.J., "Implantable Hearing Devices: State of the Art," Otolaryngologic Clinics of North America, 22:175–200, (1989).

Maniglia, M.D., A.J., et al., "A Contactless Electromagnetic Implantable Middle Ear Device for Sensorineural Hearing Loss," Ear, Nose and Throat Journal, 73(2), (1994).

Maniglia, M.D., A.J., et al., "Contactless Semi–Implantable Electromagnetic Middle Ear Device for the Treatment of Sensorineural Hearing Loss: Short–Term and Long–Term Animal Experiments," Otolaryngologic Clinics of North America, 28:121–140, (1995).

Ohno, T., "The Implantable Hearing Aid," Audecibel, Fall 1984, Winter 1985, (1984).

Snik, PhD., Ad F.M., et al., "The Bone–Anchored Hearing Aid Compared With Conventional Hearing Aids: Audiologic Results and the Patients' Opinions," Otolaryngologic Clinics of North America, 28:73–83, (1995).

Suzuki, J.I., et al., "Long–Term Clinical Results of the Partially Implantable Piezoelectric Middle Ear Implant," Ear, Nose and Throat Journal, 73(2):104–107, (Feb. 1994).

Suzuki, M.D., J.I., et al., "Partially Implantable Piezoelectric Middle Ear Hearing Device: Long–Term Results," Otolaryngologic Clinics of North America, 28:99–106, (1995).

Tjellstroöm, M.D., PhD., A., "The Bone–Anchored Hearing Aid: Design Principles, Indications, and Long–Term Clinical Results," Otolaryngologic Clinics of North America, 28:53–72, (1995).

Tos, M., et al., "Implantation of Electromagnetic Ossicular Replacement Device," Ear, Nose and Throat Journal, 73(2):92–103, (Feb. 1994).

Welling, D.B., et al., "Auditory Stimulation of the Inner Ear via the Semicircular Canals", Abstract of paper presented at International Symposium on Electronic Implants in Otology and Conventional Hearing Aids, Walt Disney World Swan, Abstract #9, (Nov. 11–14, 1993).

Yanagihara, M.D., N., et al., "Partially Implantable Hearing Aid Using Piezoelectric Ceramic Ossicular Vibrator," Abstract of Paper Presented at International Symposium on Electronic Implants in Otology and Conventional Hearing Aids. Walt Disney World Swan, Abstract #26, (Nov. 11–14, 1993).

Yanagihara, M.D., N., et al., "Partially Implantable Hearing Aid Using Piezoelectric Ceramic Ossicular Vibrator," Otolaryngologic Clinics of North America, 28:85–97, (1995).

Yanagihara, M.D., N., et al., "Development of an Implantable Hearing Aid Using a Piezoelectric Vibrator of Bimorph Design: State of the Art," Otolaryngology Head and Neck Surgery, 92:706–712, (1984).

Yanagihara, N., et al., "Implantable Hearing Aid," Archives of Otolaryngology Head and Neck Surgery, 113: 869–872, (1987).

"Middle Ear Implant: Implantable Hearing Aids," Advances in Audiology, vol. 4, M. Hoke Series Editor, Karger, 1–169, (1988).

HEARING AID TRANSDUCER SUPPORT

This is a Continuation of application Ser. No. 08/695,099 filed Aug. 7, 1996 now U.S. Pat. No. 5,836,863.

FIELD OF THE INVENTION

This invention relates to mounting implantable hearing aid transducers within the middle ear.

BACKGROUND

In an implantable hearing aid system, transducers within the middle ear engage an auditory element and transduce between electrical signals and mechanical vibrations. Middle ear hearing aid systems are not as susceptible to mechanical feedback as other types of systems. Such systems are more comfortable for the patient than other types of hearing aids, such as those placed directly in the external auditory canal. Transducers which contact an auditory element, such as one of the elements of the ossicular chain, require precise and reliable disposition within the middle ear. This is further complicated by anatomical variations among patients.

SUMMARY OF THE INVENTION

An implantable hearing aid (IHA) transducer support is mounted to the mastoid bone within a patient's middle ear region. Input and output transducers are coupled to respective mounting portions on a single support. An electronics unit of the IHA is not attached to the support, simplifying implantation and attachment of the IHA support and transducers. When repairs or adjustments, such as replacing a battery, need to be made to the electronics unit of the IHA, it is not necessary to remove or adjust the support.

In one embodiment, a support comprises a single component. Input and output transducers are coupled to respective mounting portions on opposite ends of the support prior to implantation. In a preferred embodiment, an arm extends from the support towards and into an access hole created behind the outer ear. The access hole is created, extending through the mastoid bone and into the patient's ear. The arm is attached to the mastoid bone at its proximal end, providing more stability to the support. In an even more preferred embodiment, the arm extends outside the access hole, where it is mounted subcutaneously to the mastoid bone with a bone screw or other mechanical fastener. In a further embodiment, universal connectors are placed between the support and mounting portions for each transducer. The universal connectors, such as ball and socket joints, allow further adjustability and 360 degree movement to position the transducers against respective auditory elements.

In another embodiment, the position of the transducers within the middle ear cavity may be adjusted by manipulating a mechanical fastener that affixes the support to the mastoid bone. In this embodiment, the support comprises two components. Each of the components has an opening. At least one of the openings comprises an adjustment slot. The mechanical fastener extends through mutually-aligned slots/openings on alternate support components within the middle ear region. The distance between the transducers and the angle between the transducers and the support may be independently adjusted by positioning the adjustment slots with respect to the fastener. The resulting IHA support and transducers have positional stability and are invisible externally. In a further embodiment, universal connectors are placed between mounting portions for each transducer and each respective support component. The universal connectors, such as ball and socket joints, allow further adjustability and 360 degree movement to position the transducers against respective auditory elements.

In yet another embodiment, the position of the transducers within the middle ear region may be adjusted by manipulating two mechanical fasteners. In this embodiment, the support also comprises two components. Each component of the support has at least two adjustment slots or openings. Each of the two mechanical fasteners extends through mutually-aligned openings in opposite components. At least one of the two openings, through which a mechanical fastener extends, comprises a slot. The distance between the transducers is adjusted by positioning the adjustment slots/openings with respect to their respective fasteners. The resulting IHA support and transducers also have positional stability and are invisible externally.

DETAILED DESCRIPTION

Figure 1A:
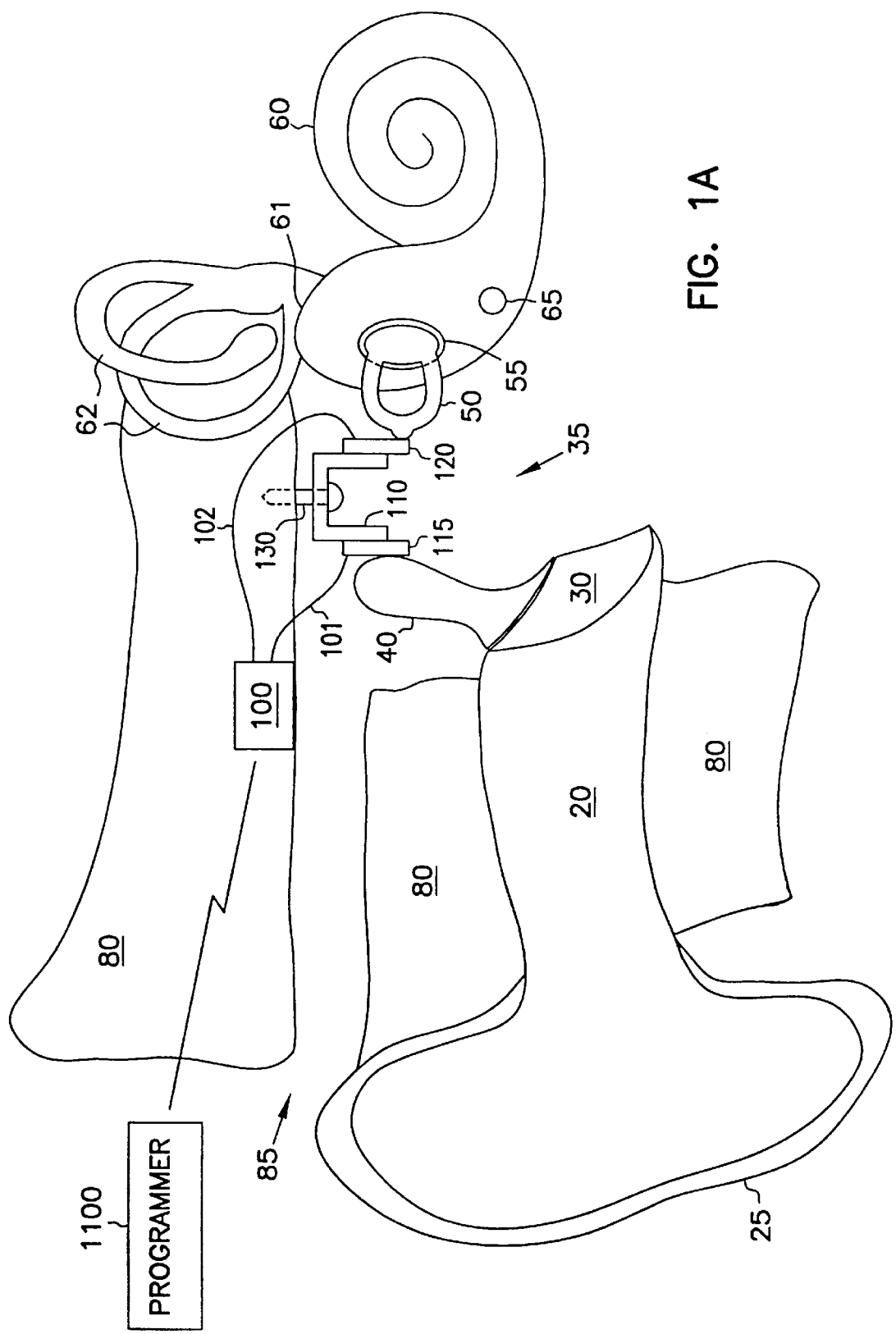
FIG. 1A is a schematic diagram illustrating a human auditory system in which an access hole is created in the mastoid, to which a single component dual transducer support is affixed.

The invention provides a transducer support, which is particularly advantageous when used in a middle ear implantable hearing aid system, such as a partial middle ear implantable (P-MEI) or total middle ear implantable (T-MEI) hearing aid system. A P-MEI or T-MEI hearing aid system assists the human auditory system in converting acoustic energy contained within sound waves into electrochemical signals delivered to the brain and interpreted as sound. FIG. 1A illustrates generally the use of the invention in a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain. Thus, the tympanic membrane 30 and ossicular chain transform acoustic energy in the external auditory canal 20 to mechanical energy at the cochlea 60.

The ossicular chain includes three primary components: a malleus 40, an incus (not shown), and a stapes 50. The malleus 40 includes manubrium and head portions. The manubrium of the malleus 40 attaches to the tympanic membrane 30. The head of the malleus 40 articulates with one end of the incus. The incus normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus articulates the capitulum of the stapes 50 to complete the mechanical transmission path.

Normally, prior to implantation of the invention, tympanic vibrations are mechanically conducted through the malleus 40, incus, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged ossicles. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses of different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing aid systems have been developed to aid patients without an intact tympanic membrane 30, upon which "air conduction" hearing aids depend. For example, temporal bone conduction hearing aid systems produce mechanical vibrations that are coupled to the cochlea 60 via a temporal bone in the skull. In such temporal bone conduction hearing aid systems, a vibrating element can be implemented percutaneously or subcutaneously.

A particularly interesting class of hearing aid systems includes those which are configured for disposition principally within the middle ear 35 space. In middle ear implantable (MEI) hearing aids, an electrical-to-mechanical output transducer couples mechanical vibrations to the ossicular chain, which is optionally interrupted to allow coupling of the mechanical vibrations to the ossicular chain. Both electromagnetic and piezoelectric output transducers have been used to effect the mechanical vibrations upon the ossicular chain.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus. Such electromagnetic output transducers have relatively high power consumption, which limits their usefulness in total middle ear implantable (T-MEI) hearing aid systems.

A piezoelectric output transducer is also capable of effecting mechanical vibrations to the ossicular chain. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain or to the oval window 55 or round window 65. In the '366 patent, the ossicular chain is interrupted by removal of the incus. Removal of the incus prevents the mechanical vibrations delivered by the piezoelectric output transducer from mechanically feeding back to the piezoelectric input transducer.

Piezoelectric output transducers have several advantages over electromagnetic output transducers. The smaller size or volume of the piezoelectric output transducer advantageously eases implantation into the middle ear 35. The lower power consumption of the piezoelectric output transducer is particularly attractive for T-MEI hearing aid systems, which include a limited longevity implanted battery as a power source.

This invention provides a support 110 for disposing transducers within the middle ear 35 for use in an implantable hearing aid (IHA). The invention is applicable for use with both P-MEI and T-MEI hearing aid systems. The support 110 is capable of carrying both input 115 and output transducers 120 on respective mounting portions. Thus, input 115 and output transducers 120 need not be separately introduced into the middle ear 35. This allows for convenient implantation of both input 115 and output transducers 120 within the middle ear 35. The electronics unit 100 of the IHA is separately implanted. This further eases implantation and repair or adjustment to the electronics unit 100 of the IHA. Maintenance and repairs, such as changing a battery in the electronics unit 100 of the IHA, are easily made without removing the support 110.

For implantation of hearing aid components, an access hole 85 is created in a region of the temporal bone known as the mastoid 80. An incision is made in the skin covering the mastoid 80, and an underlying access hole 85 is created through the mastoid 80 allowing external access to the middle ear 35. The access hole 85 is located approximately posterior and superior to the external auditory canal 20. By placing the access hole 85 in this region, transducers 15 and 120 affixed to a support 110 within the ear cavity 35 can be placed on approximately the same planar level as the auditory elements 40 and 50, which they engage.

In one embodiment, as shown in FIG. 1A, a single component support 110 is implanted into the middle ear cavity 35. Input and output transducers 115 and 120, respectively, are each affixed to the support 110 prior to implantation. One embodiment of the support 110 is illustrated generally in FIG. 1A, comprising one component. However, it is to be understood that the component can be fabricated in multiple parts and coupled together, mechanically or otherwise, to produce a single component support 110. The shape of the support 110 is not critical, provided that the support 110 allows both transducers to be mounted on it, preferably one transducer on each end. However, other configurations are possible, depending on patient anatomy and other factors. The support can be a U-shaped component, as shown in FIG. 1A, or a rectangular shaped component, among other possibilities. One consideration in determining the shape of support 110 is that the spacing between an input transducer 115 and an output transducer 120 disposed on the support 110 is approximately 10 to 20 millimeters, varying depending on the anatomical requirements of the patient.

In this embodiment, at least one input transducer 115 is affixed to a first mounting portion on a proximal end of the support 110. The input transducer 115 mechanically engages at least one auditory element, such as the malleus 40, preferably on the body of the malleus 40 at a force of approximately 10 dynes. At least one output transducer 120 is also affixed to a second mounting portion on a distal end of the support 110. The output transducer 120 is coupled to at least one auditory element, such as the stapes 50, preferably on the head of the stapes 50 at a force of approximately 10 dynes. The transducers 115 and 120 comprise any type of transducer well known to one skilled in the art. In one embodiment, transducers 115 and 120 are ceramic piezoelectric bi-element transducers. Input transducer 115 transduces mechanical energy from vibration of an auditory element, such as the malleus 40, into an electrical signal to the electronics unit 100, which is preferably implanted in the mastoid 80. The electronics unit 100 provides an amplified version of the electrical signal to the output transducer 120. In response to this amplified electrical signal, the output transducer 120 produces a resulting mechanical vibration, which is coupled to an auditory element such as the stapes 50. The electronics unit 100 is electrically connected to input transducer 115 and output transducer 120 by any convenient technique, indicated schematically as leads 101 and 102, respectively.

The support 110 is also capable of receiving at least one bone screw 130. The bone screw 130 secures the support 110 to the mastoid 80. The bone screw 130 comprises any biocompatible material, and preferably is self-tapping; if so, it is captured by the support 110 and/or an opening created by the bone screw in the mastoid 80, as well known to one skilled in the art. The support 110 also comprises any biocompatible material. Examples of biocompatible materials include titanium, stainless steel, certain ceramics (ex. alumina), certain polymers (ex. polycarbonates), and other materials well known to one skilled in the art. Furthermore, the bone screw 130 can be any type of screw well known to one skilled in the art, such as an orthopedic bone screw, a torx head screw, a single or double slotted head screw. To reduce the number of components handled during implantation of the invention, the support 110 is preferably adapted to receive and hold the bone screw 130 such that the combination can be placed against the mastoid 80 as a single unit. Any suitable known technique, such as pre-threading or otherwise shaping the support 110 in accordance with known practices, is suitable.

In this embodiment, the incus is removed to prevent feedback of mechanical vibrations from the output transducer 120 to the input transducer 115 through the incus. By affixing the support 110 to mastoid, by a bone screw 130 or other fastener, such as a biocompatible adhesive, mechanical vibrations of the output transducer 120 are not transmitted back to the input transducer 115 through the support 110.

Figure 1B:
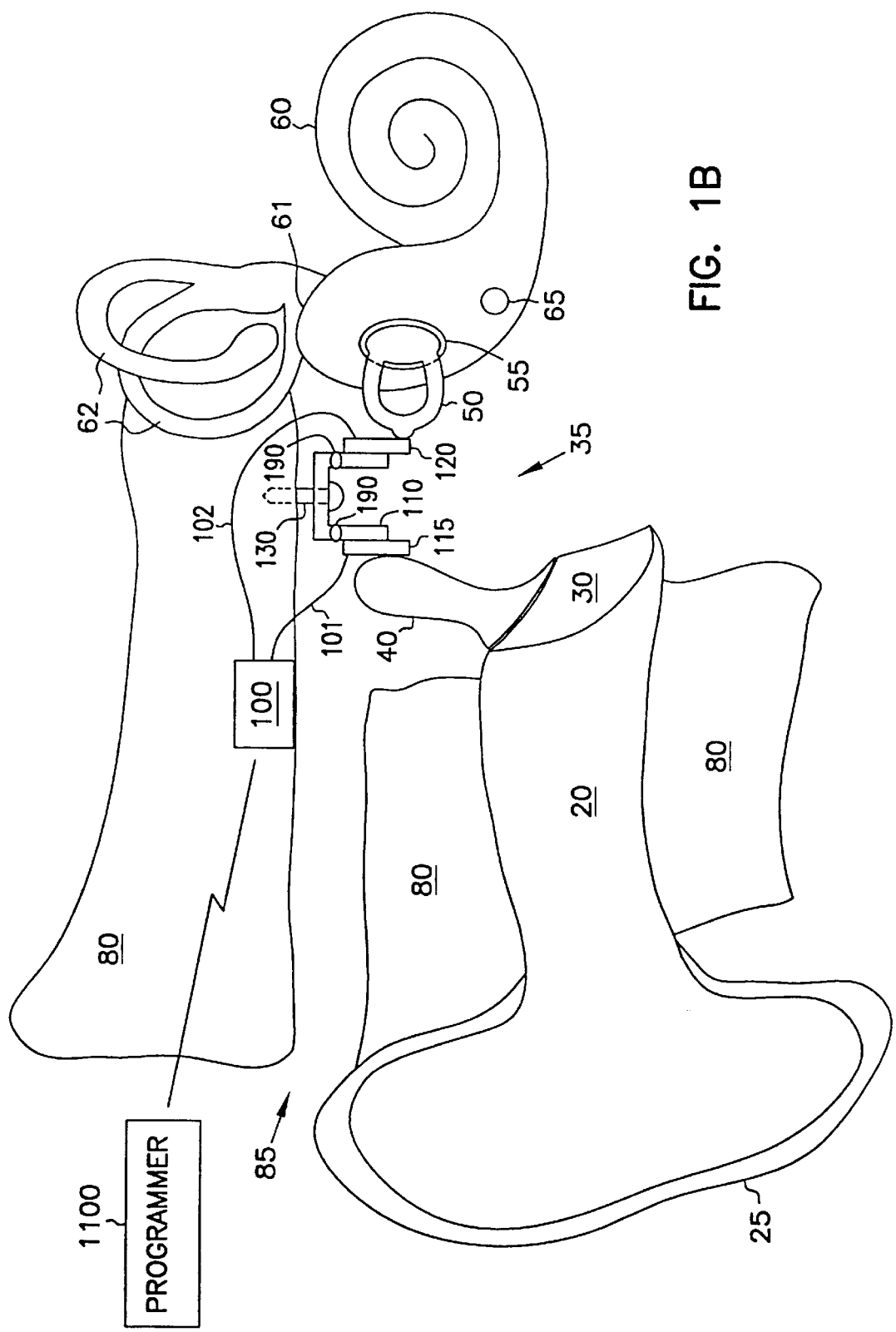
FIG. 1B is a schematic diagram illustrating a further embodiment of the invention shown in FIG. 1A, in which ball and socket joints provide further adjustability of transducer position.

In a further embodiment, as shown in FIG. 1B, universal connectors 190 are placed between mounting portions for each transducer 115, 120 and the main support 110. The universal connectors 190, such as ball and socket joints, allow further adjustability and 360 degree movement to position the transducers 115 and 120 against respective auditory elements 40 and 50.

Figure 2:
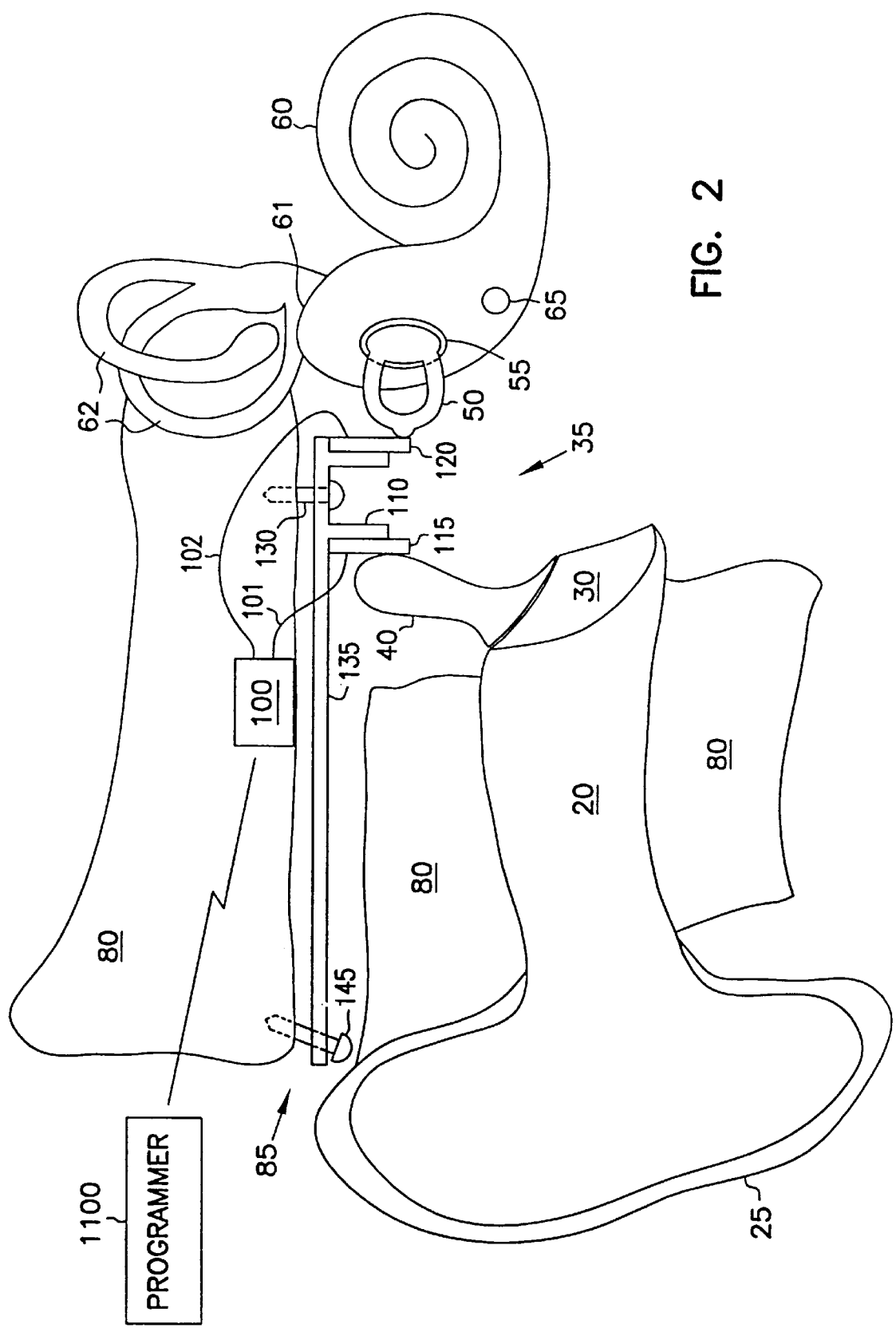
FIG. 2 is a schematic diagram illustrating a human auditory system, showing an alternate embodiment of the dual transducer support shown in FIG. 1A.

In another further embodiment, as shown in FIG. 2, the support 110 further comprises an arm 135, extending from the support 110 towards the outer ear 35 through the access hole 85. A bone screw 145 secures the arm 135 to the mastoid 80 and provides added stability to the support 110. The arm 135 comprises any biocompatible material and is approximately one inch in length, extending approximately to the entrance of the access hole 85 created behind the outer ear 25. The bone screw 145 used to affix the arm 135 to the mastoid 80 is of a similar type as the bone screw 130 used to affix the support 110 to the mastoid 80. The arm 135 also allows for easy insertion of the support 110 into the access hole 85 and the middle ear 35.

Figure 3:
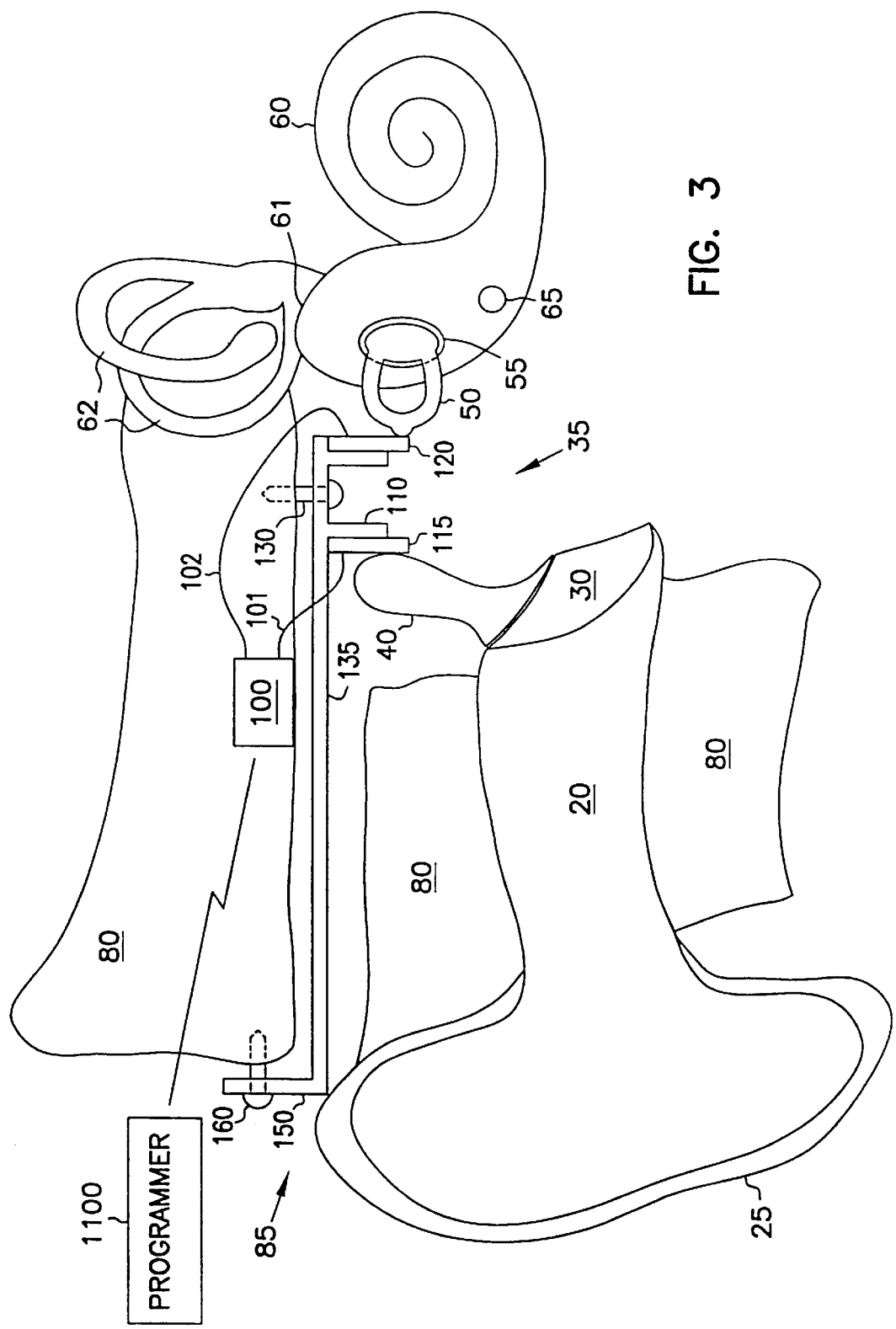
FIG. 3 is a schematic diagram illustrating a human auditory system, showing an even further embodiment of the dual transducer support shown in FIG. 1A.

In an even further embodiment, as shown in FIG. 3, the support 110 further comprises a lip 150, extending outside the entrance of the access hole 85 from the arm 135, where it is mounted subcutaneously to the mastoid bone 80 with a bone screw 160. The lip 150 extends outward radially from the proximal end of arm 135. The bone screw 160 used to attach the arm 135 to the mastoid bone 80 is of a similar type as the bone screw 130 used to attach the support 110 to the mastoid bone 80. This embodiment increases support 110 stability and eases implantation, due to the addition of the arm 135 and lip 150. However, the arm 135 can be integrally-fabricated with the lip 150, so that they are one piece as in other embodiments.

Figure 4A:
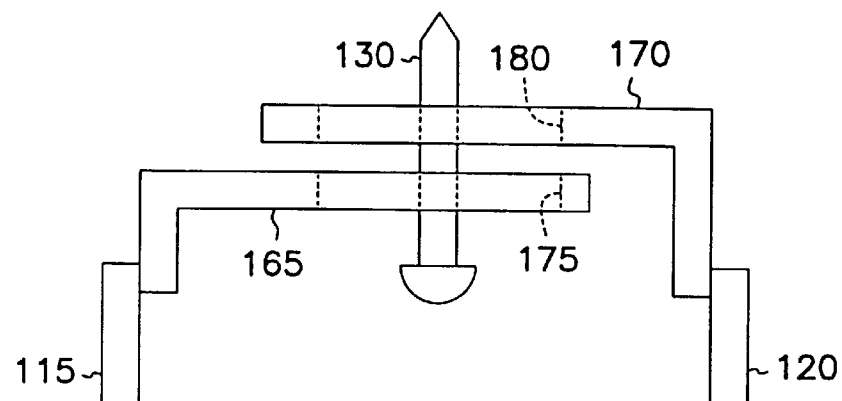
FIG. 4A is a schematic diagram illustrating yet another embodiment of a portion of the dual transducer support shown in FIGS. 1A, 2, and 3, the support having transducers affixed to opposite sides and having one mechanical fastener with adjustment slots/openings.
Figure 4B:
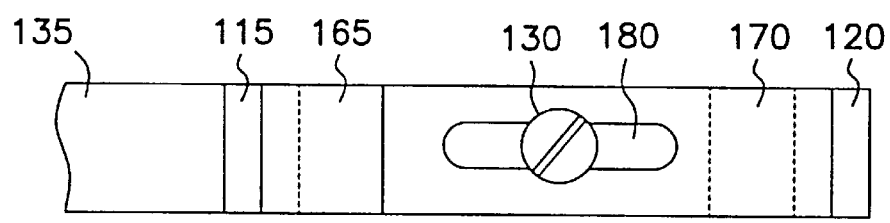
FIG. 4B is a plan view of the dual transducer support shown in FIG. 4A.

In another embodiment, the single component support 110, shown in FIGS. 1 to 3, is replaced with an adjustable support 100, having two components 170 and 165, as shown in FIGS. 4A and 4B. In this embodiment, the support 110 allows for independent adjustments of the distance between the input and output transducers 115 and 120, respectively, and the angle between the transducers 115 and 120 with respect to the support mounting screw 130. Such independent adjustments allow multiple auditory elements, such as the malleus 40 and the stapes 50, to be properly coupled to the input and output transducers 115 and 120, respectively, in a patient population having varying anatomical features within the middle ear 35.

The shape of components 165 and 170 in this embodiment is not critical, provided that the support 110 allows both transducers to be mounted on it, preferably one transducer on each end. However, other configurations are possible, depending on patient anatomy and other factors. Components 165 and 170 can be L-shaped, as shown in FIG. 4A, rectangular-shaped, or any other shape that facilitates mounting of transducers 115 and 120. Each support component 165 or 170 can be fabricated as multiple parts coupled together, mechanically or otherwise, to produce a single component 165 or 170.

A mechanical fastener, such as a bone screw 130, couples the support components 165 and 170 together and affixes the support 110 to the mastoid bone 80. However, other types of fastener techniques can be used. For example, one of the two components 165, 170 can be shaped with a flanged arm extending from it, such that the arm extends through the adjustment opening on the opposite component, coupling it with the flange. Each support component 165 and 170 has an opening 175 and 180. At least one of the openings 175, 180 comprises a slot. The bone screw 130 extends through mutually-aligned openings 175 and 180 on alternate support components 165 and 170 within the middle ear region 35. The distance between the transducers 115 and 120 and the angle between the transducers 115 and 120 with respect to the bone screw 130 are independently adjusted by positioning of the adjustment slots 175 and 180 with respect to the bone screw 130. Adjustment slots 175 and 180 operate by slidable, longitudinal positioning of support components 165 and 170 with respect to each other. The adjustment slots 175 and 180 also operate by radial positioning of each support component 165, 170 with respect to the bone screw 130. The resulting IHA support and transducers have positional stability and are invisible externally. Other types of adjustment techniques can be used in place of adjustment slots 175 and 180.

Figure 4C:
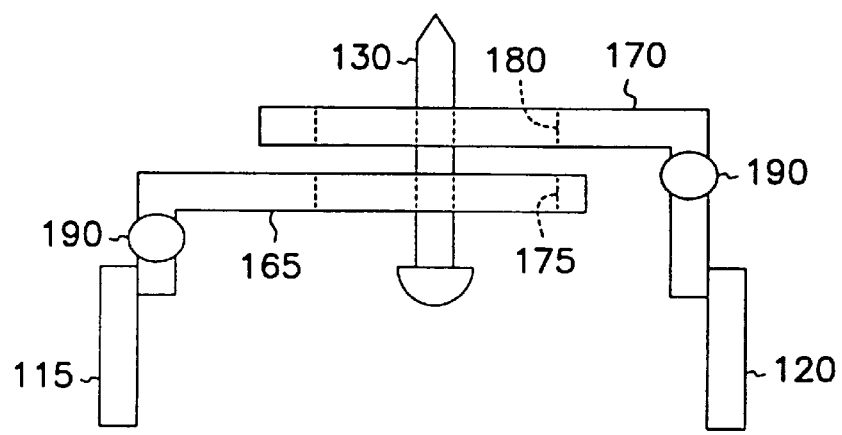
FIG. 4C is a further embodiment of the invention shown in FIG. 4A, in which ball and socket joints provide further adjustability to transducer position.

In a further embodiment, as shown in FIG. 4C, universal connectors 190 are placed between mounting portions for each transducer 115, 120 and the respective main support component 165, 170. The universal connectors 190, such as ball and socket joints, allow further adjustability and 360 degree movement to position the transducers 115 and 120 against respective auditory elements 40 and 50.

Figure 5A:
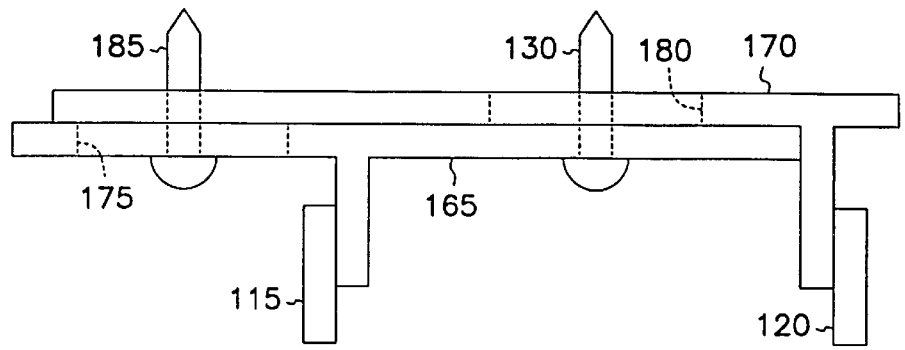
FIG. 5A is a schematic diagram illustrating yet another embodiment of a portion of the dual transducer support shown in FIGS. 1A, 2, and 3, the support having transducers attached to opposite sides and having two mechanical fasteners with adjustment slots/openings.
Figure 5B:
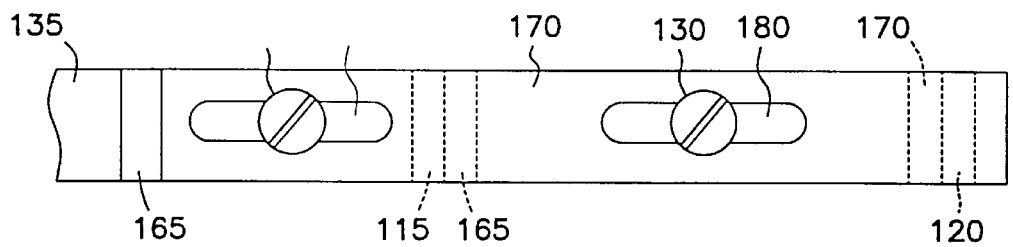
FIG. 5B is a plan view of the dual transducer support shown in FIG. 5A.

In yet another embodiment, the position of the transducers 115 and 120 is adjusted by manipulating two adjustment slots 175 and 180 within the middle ear region 35, as shown in FIGS. 5A and 5B. In this embodiment, the support also comprises two components 165 and 170. Again, each support component 165 or 170 can be fabricated in multiple parts and coupled together, mechanically or otherwise, to produce a single component 165 or 170. Each support component 165 and 170 has at least one adjustment slot 175 and 180, respectively. Two mechanical fasteners 130 and 185 extend through both support components 165 and 170 and respective mutually-aligned adjustment slots 175 and 180 on alternate support components 165, 170 within the middle ear region 35. The distance between the transducers 115 and 120 is adjusted by positioning of the adjustment slots 175 and 180. The resulting IHA support and transducers also have positional stability and are invisible externally.

The shape of the two support components 165 and 170 in this embodiment is not critical, provided that the support 110 allows both transducers 115 and 120 to be mounted on it, preferably one transducer 115, 120 on each end. However, other configurations are possible, depending on patient anatomy and other factors. Each component 165, 170 can be L-shaped, modified L-shaped, as shown in FIG. 5A, rectangular-shaped, or any other shape that facilitates mounting of transducers 115 and 120 to the support 110. A bone screw 130 couples the two components 165 and 170 together and affixes the support 110 to the mastoid bone 80, through an adjustment slot 180 on one component 170. Another screw 185 couples the support components 165 and 170 together through a second adjustment slot 175. This screw 185 comprises a similar material as the bone screw 130 that affixes the support 110 to the mastoid 80, and it can also attach to the mastoid bone 80 for added stability. The distance between the transducers 115 and 120 is adjusted by positioning of the adjustment slots 175 and 180. The adjustment slots 175 and 180 operate by allowing slidable, longitudinal positioning of the two components 165 and 170 with respect to each other. Depending on the fabrication of the components 165 and 170 and their respective adjustment slots 175 and 180, the distance between the transducers 115 and 120 is adjustable by approximately 5 millimeters in either direction. The resulting IHA support and transducers have positional stability and are invisible externally. As with other embodiments, other types of adjustment techniques can be used in place of adjustment slots 175 and 180.

Figure 5C:
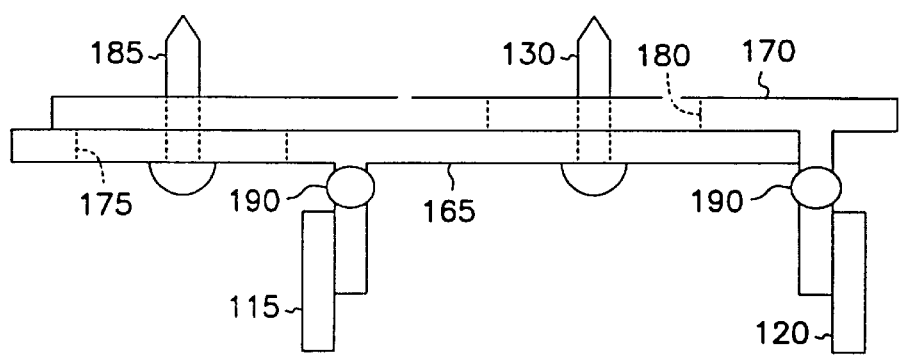
FIG. 5C is a further embodiment of the invention shown in FIG. 5A, in which ball and socket joints provide further adjustability to transducer position.

In a further embodiment, as shown in FIG. 5C, universal connectors 190 are placed between mounting portions for each transducer 115, 120 and the respective main support component 165, 170. The universal connectors 190, such as ball and socket joints, allow further adjustability and 360 degree movement to position the transducers 115 and 120 against respective auditory elements 40 and 50.

We claim:

1. A method of mounting an implantable and configurable support member in a patient's middle ear comprising the steps of:

passing the support member in a first configuration through an external access to a location in the patient's middle ear;

reconfiguring the support member to a second configuration, thereby forming a shape which is different from said first configuration;

mounting a plurality of transducers to the support member after the support member has passed through the external access; and mounting the support member in the patient's middle ear.

2. The method of claim 1, wherein the reconfiguring step comprises positioning a first transducer against a first auditory element and positioning a second transducer proximate a second auditory element.

3. The method of claim 1, in which reconfiguring step further comprises adjusting at least one universal connector of the support member.

4. The method of claim 1, in which the reconfiguring step takes place in the patient's middle ear.

5. The method of claim 1, in which the reconfiguring step further comprises adjusting a plurality of slots defined in the support member.

6. The method of claim 1, in which the mounting step further comprises mounting the support member to the patient's mastoid.

7. The method of claim 1, in which the passing step further comprises providing the support member as a plurality of components.

* * * * *